United States Patent [19]

Crider

[11] Patent Number: 4,539,118

[45] Date of Patent: Sep. 3, 1985

[54] RAPID, ACCURATE METHOD OF SEPARATION OF OXALATE FROM URINE AND OTHER BIOLOGICAL FLUIDS

[75] Inventor: Quincy E. Crider, Kirkwood, Mo.

[73] Assignee: Sigma Chemical Company, St. Louis, Mo.

[21] Appl. No.: 592,950

[22] Filed: Mar. 23, 1984

[51] Int. Cl.$^3$ ............................................. B01D 15/04
[52] U.S. Cl. .................................. 210/683; 210/691; 210/692; 210/927
[58] Field of Search ............... 210/683, 691, 692, 662, 210/670, 673, 908, 927

[56] References Cited

U.S. PATENT DOCUMENTS 3,920,397  11/1975  Small et al. ......................... 210/683

FOREIGN PATENT DOCUMENTS 2806371  8/1979  Fed. Rep. of Germany .
54-43797  6/1979  Japan .

OTHER PUBLICATIONS

Buttery, J. E. et al., "Determination of Urinary Oxalate with Commercially Available Oxalate Oxidase", Clin. Chem., vol. 29, pp. 700–702, (1983).
Hodgkinson, A. et al., "An Improved Colorimetric Procedure for Urine Oxalate", Clinica Chimica Acta, vol. 36, pp. 127–132, (1972).
Krugers Dagneaux, P.G.L.C. et al., "Oxalic Acid Determination in Plasma", Clinica Chimica Acta, vol. 71, pp. 319–325, (1976).
Laker, M. F. et al., "Spectrophotometric Determination of Urinary Oxalate with Oxalate Oxidase Prepared from Moss", Clin. Chem., vol. 26, pp. 827–830, (1980).
Lartillot, Serge et al., "Determination of Oxalic Acid in Serum by a Colorimetric Enzymic Method", Feuill. Biol., vol. 22, No. 119, pp. 53–57, (1981).
Lartillot, Serge et al., "Oxalic Acid Determination in Urine and Urinary Calculi by a Colorimetric Enzymic Method", Feuill. Biol., vol. 21, No. 115, pp. 43–48, (1980).

*Primary Examiner*—Ivars Cintins
*Attorney, Agent, or Firm*—Arthur S. Morgenstern

[57] ABSTRACT

A novel technique has been discovered for separating oxalate from urine and other biological fluids. The method involves mixing the fluid with an adsorbent to separate the oxalate from the fluids, washing the adsorbent-oxalate complex, and releasing the oxalate by reacting the complex with alkali. This technique provides accurate results and can easily be run in hospitals and clinical laboratories.

20 Claims, No Drawings

RAPID, ACCURATE METHOD OF SEPARATION OF OXALATE FROM URINE AND OTHER BIOLOGICAL FLUIDS

BACKGROUND OF THE INVENTION

Up until now the analysis of oxalate in biological fluids has been difficult and time-consuming. The other chemicals present in the fluids interfere with oxalate determination. As a result, it was necessary to separate the oxalate by using a precipitant, by passing the fluid through an ion exchange resin, or by some other technique. The isolated oxalate could then be quantified by using one of several known techniques. These isolation techniques, due to the several steps involved, introduced experimental error that affected accuracy of the results.

Other techniques have attempted to avoid separation of oxalate, by such means as creation of a "blank" to compensate for the other chemicals present. These techniques have not been successful in compensating for contaminants, and results have been inaccurate.

SUMMARY OF THE INVENTION

The present invention is an accurate and rapid technique for separating oxalate from biological fluids. It involves mixing the biological fluid with an adsorbent which binds the oxalate, washing the adsorbent, then eluting off the oxalate with alkali. The resulting oxalate can be quantified by using one of the known methods for oxalate analysis.

This invention is easy to use in any laboratory and is rapid enough to be routinely used in a hospital or clinical laboratory.

OXALATE IN BIOLOGICAL FLUIDS

Oxalate is normally excreted in small quantities in the urine. However, the ingestion of large amounts of oxalate rich foods, such as as spinach, chocolate or rhubarb, or oxalate precursors, such as ascorbic acid, will result in significant increases in urinary oxalate excretion.

Oxalate concentration may be an indicator of certain diseases, such as primary hyperoxaluria, cirrhosis, occurrence of renal calculi, tubular acidosis, and sarcoidosis. These and other diseases make it important for the physician to be able to determine oxalate concentration in body fluids.

The analysis of oxalate is complicated by the fact that other chemicals which appear in biological fluids interfere with the analysis of oxalate. Most commonly used procedures employ some means of extracting or isolating oxalate from urine before assay. Isolation procedures include precipitating the oxalate with calcium, ion exchange chromatography or preparing a derivative of oxalate for separation on high pressure liquid chromatographic equipment. All the above procedures are very lengthy and most require expensive equipment not commonly found in the clinical laboratory.

DESCRIPTION OF THE INVENTION

This technique is very simple and rapid, and it can be conducted in any laboratory. Moreover, the extraction procedure provides complete extraction of oxalate. Unless extreme precautions are taken, other isolation procedures do not provide acceptable recovery.

This invention utilizes adsorbents to mix with biological fluids and separate the oxalate from the balance of the components. In this procedure, adsorbent is combined with a biological fluid, swirled, and the adsorbent along with the adsorbed oxalate is allowed to settle. The supernatant is discarded. The adsorbent-oxalate complex is washed with water and swirled, and the complex is allowed to settle. The water supernatant is also discarded. The adsorbent-oxalate complex is then treated with alkali, swirled, and the adsorbent is allowed to settle. The supernatant containing the oxalate is decanted and used for analysis. The resulting solution may be assayed using one of the several techniques available for quantifying oxalate.

Among the adsorbents that can be used in this invention are amphoteric adsorbents (such as aluminum oxide (alumina); magnesium silicate; silica gel; calcium phosphate; crystalline, hydrated alkali-aluminum silicate; and hydroxylapatite) and anion exchange adsorbents (such as diethylaminoethyl cellulose and trimethyl benzyl ammonium polystryrene).

Several examples will be shown below which show that the technique can be used to analyze for oxalate at several levels (normal and elevated) and that the technique gives results which are equivalent to other, more time consuming techniques.

EXAMPLE 1

A 24 hour urine specimen was collected in a container containing 10 mL of concentrated hydrochloric acid. The total volume of urine collected was measured so that oxalate excretion over a 24-hour period could be determined. The urine sample was swirled to make sure that it was uniform, and a 1.0 mL sample was withdrawn and added to 150 mg of aluminum oxide (alumina) in a small test tube. The tube was capped and the urine and alumina were mixed for 5–6 minutes at room temperature. The adsorbent was allowed to settle, and the supernatant was discarded. 2 mL of water was added to the alumina, and it was shaken and the alumina allowed to settle. The water was discarded. 1 mL of 0.2 normal sodium hydroxide was added to the capped vial containing alumina, mixed for 5–6 minutes at room temperature, and the adsorbent was allowed to settle. The extract was transferred to a clean vial for subsequent assay. The supernatant was analyzed by reacting the oxalate with 3-(dimethylamino)-benzoic acid (DMAB), peroxidase, oxalate oxidase, and 3-methyl-2-benzothiozolinone hydrazone (MBTH). The absorbance of the solution was measured at 590 nm and compared with that of a standard solution. The oxalate concentration, since its absorbance follows Beers Law, can be determined using the formula:

$$\frac{\text{Absorbance of Test}}{\text{Absorbance of Standard}} \times \text{concentration of standard} = \text{concentration of test sample}$$

The oxalate value determined was then adjusted to allow for the total urine collected in 24 hours. The resulting number was used to determined whether oxalate concentration was normal or higher than normal.

EXAMPLE 2

A urine specimen was assayed for oxalate by the technique used in Example 1 and found to contain 31 mg/24 hr. That same specimen was assayed by a method utilizing calcium precipitation to separate the oxalate and titration of oxalate with potassium permanganate. The specimen was found to contain 29 mg/24 hrs using this technique.

EXAMPLE 3

A urine specimen was assayed for oxalate by the technique in Example 1 (and found to contain 36 mg/24 hr) and by a technique using oxalate decarboxylase and formate dehydrogenase (where the oxalate content was found to be 33 mg/24 hr). The oxalate decarboxylase method requires long testing time and cannot be automated.

EXAMPLE 4

A urine specimen from a "normal" patient was assayed for oxalate by the technique used in Example 1, but the adsorbent was trimethyl benzyl ammonium polystyrene. The same sample was analyzed by using an ion exchange column to isolate the oxalate and by a technique using high pressure liquid chromatography. The results from the two analyses were 20 mg of oxalate per 24 hours.

EXAMPLE 5

A pathological urine specimen was assayed for oxalate by the technique described in Example 1 and found to contain 115 mg per 24 hours. That same sample was analyzed and by a technique requiring the use of oxalate decarboxylase which evolves $CO_2$. The results from this second technique were found to be equivalent. Special equipment not commonly found in a clinical lab is required for the latter technique.

EXAMPLE 6

"Normal" urine specimens were assayed for oxalate by the technique used in Example 1, but the adsorbent was crystalline, hydrated alkali-aluminum silicate. The specimens were found to contain 10 to 30 mg/24 hours.

The foregoing examples are merely illustrative of the present invention.

What is claimed is:

1. A method for separating oxalate from body fluids, which comprises:
   (a) Mixing the body fluid with an adsorbent or a combination of adsorbents,
   (b) Swirling the mixture and allowing the adsorbent to settle, discarding the supernatant,
   (c) Washing the adsorbent by swirling with water, allowing the adsorbent to settle, discarding the supernatant,
   (d) Adding alkali to the adsorbent, mixing, allowing the adsorbent to settle, and decanting the supernatant for use in analyzing for oxalate.

2. A method according to claim 1, where the adsorbent is an amphoteric adsorbent.

3. A method according to claim 1 where the adsorbent is an anion exchange adsorbent.

4. A method according to claim 1, where the adsorbent is aluminum oxide.

5. A method according to claim 1, where the adsorbent is magnesium silicate.

6. A method according to claim 1, where the adsorbent is silica gel.

7. A method according to claim 1, where the adsorbent is crystalline, hydrated alkali-aluminum silicate.

8. A method according to claim 1, where the adsorbent is hydroxylapatite.

9. A method according to claim 1, where the adsorbent is diethylaminoethyl cellulose.

10. A method according to claim 1, where the adsorbent is trimethyl benzyl ammonium polystyrene.

11. A method for separating oxalate from urine, which comprises:
    (a) Mixing the urine with an adsorbent or a combination of adsorbents,
    (b) Swirling the mixture and allowing the adsorbent to settle, discarding the supernatant,
    (c) Washing the adsorbent by swirling with water, allowing the adsorbent to settle, discarding the supernatant,
    (d) Adding alkali to the adsorbent, mixing, allowing the adsorbent to settle, and decanting the supernatant for use in analyzing the oxalate.

12. A method according to claim 11, where the adsorbent is an amphoteric adsorbent.

13. A method according to claim 11, where the adsorbent is anion exchange adsorbent.

14. A method according to claim 11, where the adsorbent is aluminum oxide.

15. A method according to claim 11, where the adsorbent is magnesium silicate.

16. A method according to claim 11, where the adsorbent is silica gel.

17. A method according to claim 11, where the adsorbent is crystalline, hydrated alkali-aluminum silicate.

18. A method according to claim 11, where the adsorbent is hydroxylapatite.

19. A method according to claim 11, where the adsorbent is diethylaminoethyl cellulose.

20. A method according to claim 11, where the adsorbent is trimethyl benzyl ammonium polystyrene.

* * * * *